United States Patent
Burkinshaw

(10) Patent No.: US 8,926,699 B2
(45) Date of Patent: Jan. 6, 2015

(54) COMPOSITE BONE GRAFT KIT

(75) Inventor: Brian Burkinshaw, Pflugerville, TX (US)

(73) Assignee: SpineSmith Partners, LP, Austin, TX (US)

( * ) Notice: Subject to any disclaimer, the term of this patent is extended or adjusted under 35 U.S.C. 154(b) by 0 days.

(21) Appl. No.: 13/360,694

(22) Filed: Jan. 28, 2012

(65) Prior Publication Data

US 2013/0030547 A1    Jan. 31, 2013

Related U.S. Application Data

(60) Provisional application No. 61/462,096, filed on Jan. 28, 2011.

(51) Int. Cl.
| | |
|---|---|
| *A61F 2/28* | (2006.01) |
| *A61L 27/36* | (2006.01) |
| *A61F 2/46* | (2006.01) |
| *A61F 2/30* | (2006.01) |
| *A61F 2/44* | (2006.01) |

(52) U.S. Cl.
CPC ............... *A61F 2/28* (2013.01); *A61L 27/3608* (2013.01); *A61L 27/365* (2013.01); *A61F 2/4644* (2013.01); *A61F 2002/2835* (2013.01); *A61F 2002/30909* (2013.01); *A61F 2/44* (2013.01); *A61F 2002/4495* (2013.01); *A61F 2310/00293* (2013.01); *A61F 2310/00359* (2013.01); *A61L 2430/02* (2013.01)
USPC ...................... 623/16.11; 623/23.61

(58) Field of Classification Search
CPC ........................................................ A61F 2/28
USPC ................ 623/16.11, 23, 51, 23.61, 23.64
See application file for complete search history.

(56) References Cited

U.S. PATENT DOCUMENTS

| | | | | |
|---|---|---|---|---|
| 2003/0039676 A1* | 2/2003 | Boyce et al. | ................. | 424/423 |
| 2008/0269893 A1* | 10/2008 | Bhatnagar et al. | ......... | 623/11.11 |
| 2009/0024224 A1* | 1/2009 | Chen et al. | ................. | 623/23.72 |
| 2009/0157087 A1* | 6/2009 | Wei et al. | ........................ | 606/99 |
| 2009/0157182 A1* | 6/2009 | Koblish et al. | ............. | 623/16.11 |

* cited by examiner

*Primary Examiner* — Jason-Dennis Stewart
(74) *Attorney, Agent, or Firm* — Winstead PC

(57) ABSTRACT

A composite bone graft which comprises an allograft bone component; a synthetic bone substitute, wherein the synthetic bone substitute is in contact with the allograft bone component. The composite is arranged in a core/outer layer structure.

7 Claims, 3 Drawing Sheets

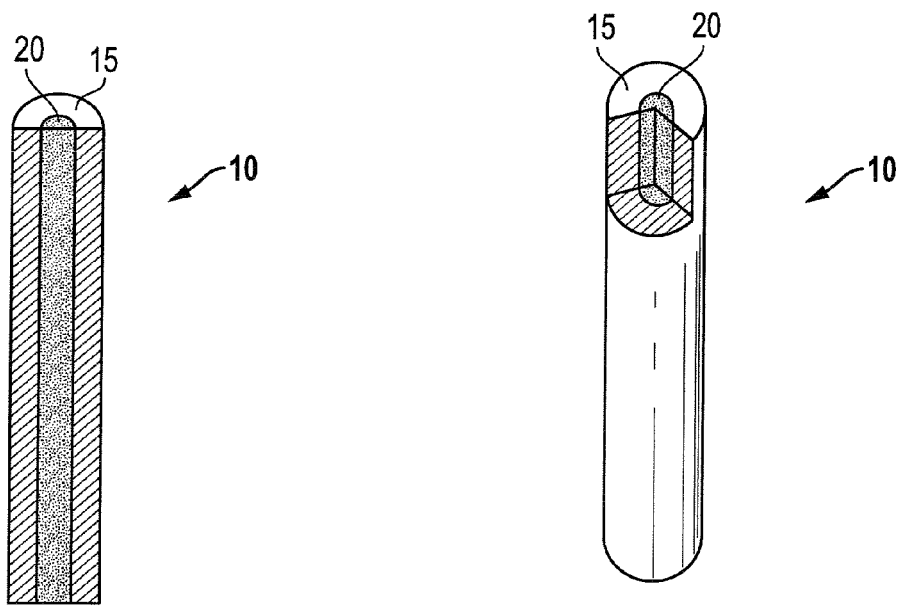
FIG. 1
FIG. 2
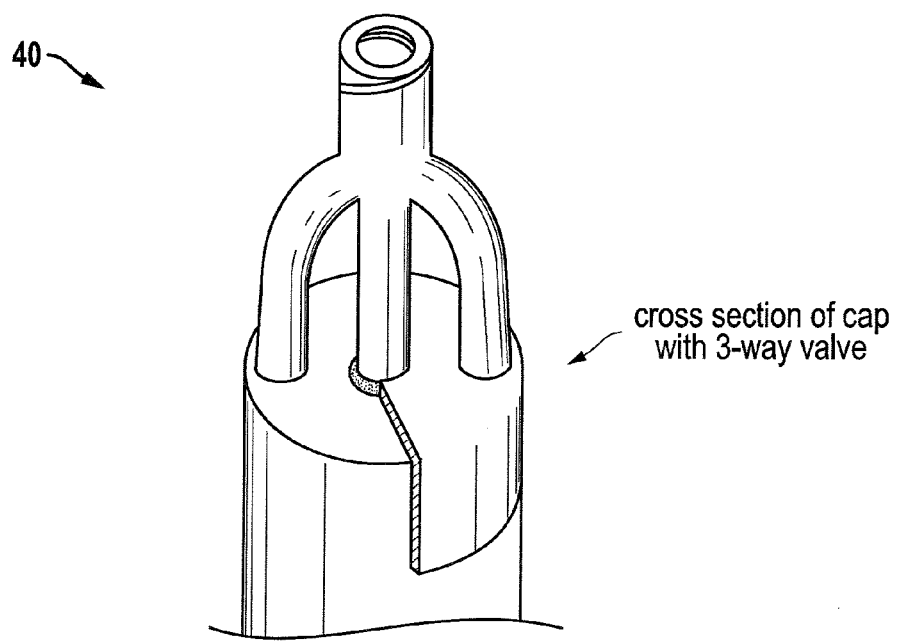
FIG. 4

COMPOSITE BONE GRAFT KIT

This applications claims priority to U.S. provisional application Ser. No. 61/462,096, filed Jan. 28, 2011, incorporated herein in its entirety by reference.

FIELD OF THE INVENTION

The invention herein relates generally to the field of spinal fusion. In particular, this invention is drawn to a bone graft delivery kit and associated methods of use.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine (or fuse) two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae, reestablishing normal spinal column height and lordosis, and relieving pressure on spinal nerve roots. Conditions for which spinal fusion might be done include degenerative disc disease, treatment of a spinal tumor, a vertebral fracture, scoliosis, herniation of the disc, spondylolisthesis, or any other condition that causes instability of the spine.

As a part of the procedure, bone or bone substitute grafts are commonly placed between the vertebrae following excision of the degenerated spinal disc, and topically along the posterolateral portion of the spine, adjacent to the degenerated segment. This helps induce bone growth between two adjacent vertebrae and fuses the facets in the posterior spinal segments. Currently available synthetic bone grafts, however, are typically not optimal and natural autologous bone grafts are in limited in supply, while cadaveric or allograft bone grafts carry a risk of disease transmission. These grafts often collapse and/or resorb too quickly, even in the presence of supplemental proteins such as BMP, to encourage sufficient bone growth or good quality, healthy bone formation.

There is therefore a need for a bone graft that adequately promotes spinal fusion to treat degenerative disc disease and other spinal conditions, while providing improvements over the prior methods.

SUMMARY OF THE INVENTION

This invention provides a solution to the problems and disadvantages described above by providing a combined synthetic and natural bone matrix that promotes a solid fusion, controlled resorption of the matrix, and regeneration of a new fusion mass.

In one broad respect, this invention is a composite bone graft which comprises an allograft bone component and a synthetic bone substitute, wherein the synthetic bone substitute is in contact with the allograft bone component. The composite may include a mesh casing, wherein the allograft bone component and the synthetic bone substitute are disposed through (encased within) the mesh casing. In general, the graft is in the form of a cylinder with an inner core and outer layer, and in one embodiment the inner core is 5 to 15 mm in diameter and the outer layer is 2 to 15 mm in thickness. In one embodiment, the inner core is composed of the allograft bone component and the outer layer is composed of the synthetic bone substitute. In another embodiment, the inner core is composed of the synthetic bone substitute and the outer layer is composed of the allograft bone component. In one embodiment, the allograft bone component and synthetic bone substitute are at least partially infused with an additive, wherein the additive is one or more of platelet rich plasma, bone marrow aspirate, stem cells or other additive. In one embodiment, the composite bone graft is positioned within a bone graft syringe. The synthetic bone substitute can be, for example, beta-tricalcium phosphate, hydroxyapetite, polyglycolic-polylactid acid. or poly-lactic acid. The allograft bone can be in the form of dense cortical bone strips, packed bone chips, or demineralized bone matrix.

In another broad respect, this invention is a method of manufacturing a composite bone graft, comprising forming an inner core and forming an outer layer of a different component around the inner layer. The inner core can be made of allograft bone component and the outer layer can be made of a synthetic bone substitute. Alternatively, the inner core can be made of a synthetic bone substitute and the outer layer can be made of a allograft bone component.

In another broad respect, this invention is a method for using a composite bone graft which comprises providing a bone graft syringe having a composite bone graft disposed within the bone graft syringe; connecting the bone graft syringe to a delivery syringe, wherein the delivery syringe is further described as containing an injectable component selected from the group consisting of a cell concentrate, a platelet rich plasma, a bone marrow aspirate, a clotting agent, and mixtures thereof; injecting the injectable component into the bone graft syringe; and expelling the composite bone graft and the injectable component from the bone graft syringe. This method can include the step of filling a mesh casing with a composite bone graft.

In another broad respect, this invention is a composite bone graft kit which comprises a bone graft syringe and a composite bone graft disposed within the bone graft syringe, wherein the composite bone graft is further defined as having an allograft bone component and a synthetic bone substitute component. The kit can include a mesh casing. The kit can also include a delivery syringe that connects to the bone graft syringe for delivery of an injectable fluid such as cell concentrate, a platelet rich plasma, a bone marrow aspirate, a clotting agent, and mixtures thereof. Thus, the kit can also include platelet rich plasma, bone marrow aspirate, stem cells, and combinations thereof.

In another broad respect, this invention is a method of treating a spine, comprising: applying topically a bone graft composite to a posterolateral portion of a spine. Alternatively, the bone graft composite is applied to an inner void of a fusion device, or applied to both a spine and an inner void of a fusion device. The bone graft composite can be applied by ejecting the bone composite graft from a bone graft syringe.

BRIEF DESCRIPTION OF THE DRAWINGS

The specific features, aspects, and advantages of the present invention will become better understood with regard to the following description, appended claims, and accompanying drawings where:

FIGS. 1 and 2 illustrate cross-sectional views of cylindrical composite graft.

FIGS. 4 and 5 illustrate a cross sectional view and a perspective view of a removable cap used in conjunction with a secondary syringe for infusing a composite bone graft with an additive.

DETAILED DESCRIPTION OF THE INVENTION

Figure 3:
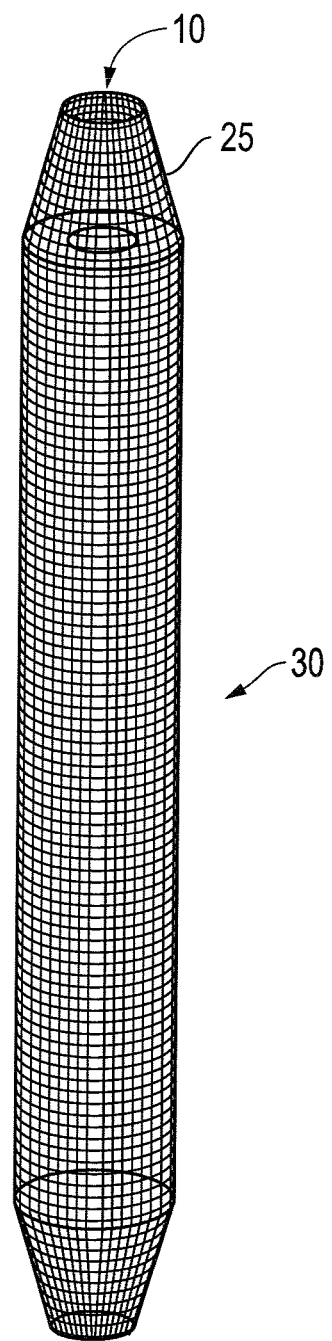
FIG. 3 illustrates a cylindrical composite graft encased in an absorbable mesh sheath.
Figure 5:
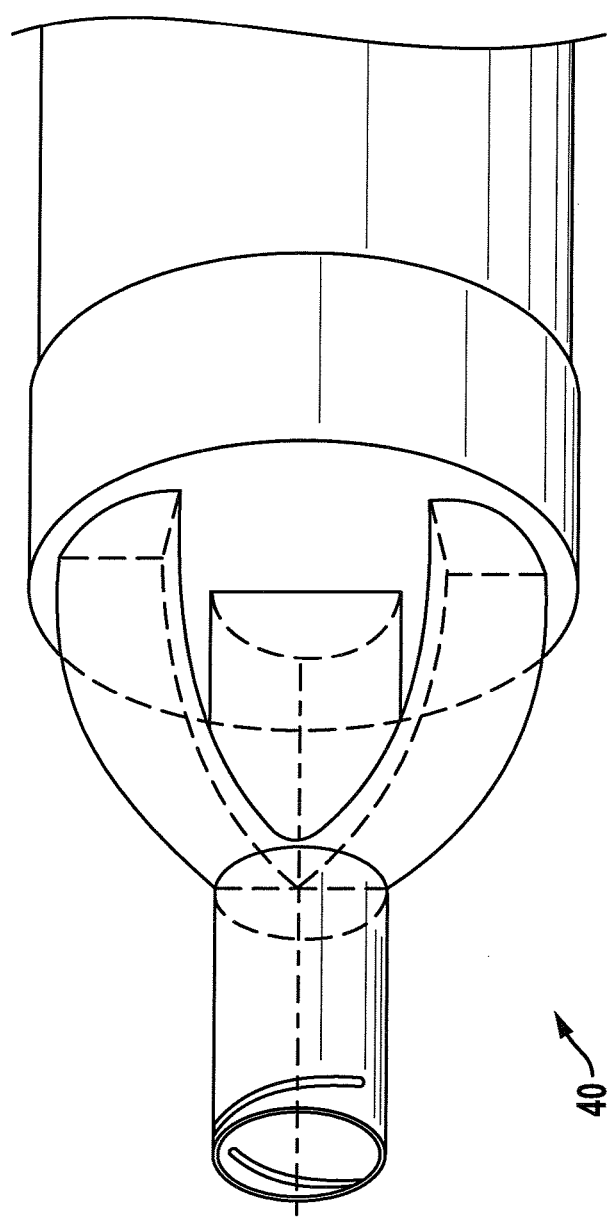

The present invention relates a composite bone graft, composite bone graft delivery kit and method for use.

Composite Bone Graft

The composite graft combines allograft or autograft bone and a synthetic bone substitute to form a composite graft that can be used as a topical onlay for fusion grafting in, for example, the posterolateral gutters of the spine, across a fusion segment. The composite graft is formed prior to introduction into or onto the patient.

In one embodiment, the inner core of the graft may comprise a synthetic bone substitute materials (which are sometimes referred to as bone scaffold materials), such as beta-tricalcium phosphate (BTCP), hydroxyapetite, polyglycolic-polylactid acid (PGLA), poly-lactic acid (PLA), or other synthetics. Allograft or autograft bone may be packed around the synthetic core. The composite is typically formed in concentric cylindrical shells. In one embodiment, the inner cylindrical shell is removed after the core and surrounding have been packed. The allograft bone may take the form of dense cortical bone strips, packed bone chips, demineralized bone matrix, or other allograft bone formations. This composite graft may be soaked with platelet rich plasma, bone marrow aspirate, and/or stem cells. The composite may also be treated with an appropriate supplemental clotting agent, such as thrombin or a solution containing $CA^+$ ions, to bind the composite graft together.

Alternatively, a composite graft may comprise an allograft or autograft bone inner core. This inner core may take the form of dense cortical bone strips, packed bone chips, demineralized bone matrix, or other allograft bone formations. A synthetic bone substitute, in the form of compressed granules, strips, a pre-formed cylinder or powder, may be distributed around the outside of the allograft core. This composite graft may be soaked with platelet rich plasma, bone marrow aspirate, and/or stem cells. The composite may also be treated with an appropriate clotting agent, such as thrombin or a solution containing calcium ions, to bind the composite graft together.

A composite graft provides a stronger construct than traditional bone grafts with the potential for slower resorbsion and better bone formation. The synthetic core, or synthetic outer cylinder may be designed to have high surface area porosity or micro-channels to mimic natural cancellous bone structure. In general, a high surface area is a greater than 3 fold increase in surface area over a traditionally used calcium phosphate. Traditional calcium phosphates have a surface area of 1 $m^2$/gram. A cancellous bone structure permits bone marrow to enter the center of the bone graft. These characteristics provide for a composite bone graft that can be constructed to mimic natural bone having a cortical outer layer, a cancellous inner layer, and a bone marrow center.

A combination of synthetic and allograft or autograft bone materials helps control resorption of the composite graft and improves the longevity of the graft. These properties also help encourage bone growth. The composite graft facilitates stem cell differentiation and formation of a highly vascularized bone structure at an early stage of remodeling, while maintaining a more stable structure for a longer period of time to promote better fusion.

A cross-sectional view of a composite 10 is shown in FIGS. 1 and 2. The composite includes an outer layer 15 and inner core 20.

In another embodiment, the composite bone graft may be captured in a resorbable mesh casing. See in this regard FIG. 3. In FIG. 3, the composite bone graft 10 is surrounded by a resorbable mesh casing 25 to create a mesh encased composite bone graft 30. The mesh may help hold the composite together and reduce the potential for the composite graft to dissipate prematurely or break apart before bone can form. The mesh may also be used to anchor the composite graft above and below the fusion site using suitable attachment means such as bone anchors or screws. The mesh casing would typically be about the same size as the syringe; however, it will be elongated when pulled putting the casing and graft in tension. The resorbable mesh casing may take the form of a "Chinese finger trap," such that the diameter of the casing lessens as the ends of the casing are pulled, such as described in in U.S. Pat. No. 6,602,290, incorporated herein by reference. Any biodegradable, biocompatible polymer or copolymers, having resorbable properties may be used to construct the casing. For example, PLA (polylactide), PGLA (copoly lactic acid/glycolic acid), and PLLA (poly-l-lactide) are representative possible casing compositions. The configuration of the weave or the material composition may be varied to control resorption. The composite bone graft may have an allograft, or autograft inner core, or the synthetic bone substitute material.

Composite Bone Graft Kit

A composite bone graft kit may comprise a conventional bone graft syringe containing a synthetic core within the syringe body. A bone syringe is typically about 1.5 cm in diameter and 10 cm in length. Depending on the addition of diluents for clotting and cell adhesion, the composite is typically expelled allowing it to maintain a cylindrical shape as it fills the casing or is cut to desired length. The synthetic core may be surrounded by bone chips or other autograft or allograft bone components. As an example, the syringe may carry a 5-15 mm diameter synthetic core surrounded by a 2-15 mm thick bone chip outer layer. The resulting construct can have a total diameter of from 7 mm to 3 cm. In certain embodiments, the core has a diameter of 5-10 mm or 10-15 mm. In certain embodiments, the outer layer has a diameter of 2-5 mm or 5-15 mm. For example, the volume of the composite can be about 75 percent core and 25 percent outer layer. The total amount of bone graft composite to be delivered in the syringe is typically 15 to 20 cubic centimeters (cc). In general the composite has a length in the syringe of from 8 to 10 centimeters (cm). As applied the composite may cover a wide variety of surface sizes. In one embodiment, the core more similarly relates to cortical bone with the core more similarly relating to cancellous bone, thus defining to different, defined regions of the composite, as contrasted with an admixture. The proportions and quantity of synthetic and allograft bone material may vary. Alternatively, the kit may comprise a bone graft syringe comprising an autograft or allograft bone core surrounded by a synthetic material.

In one embodiment, at least one end of the syringe has a mechanism to allow platelet rich plasma, bone marrow aspirate, stem cells, and/or clotting agent(s) to enter the syringe and soak the composite graft. For example, a removable cap may be positioned at one end of the syringe. The cap may contain one or more ports for the sequential or simultaneous injection of one or more components (additives such as platelet rich plasma) from a secondary source. See in this regard, FIG. 4 and which depict a removable cap 40 that includes a 3 way valve (multi-lumen port) that corresponds to three channels for injection of the platelet rich plasma, bone marrow aspirate, stem cells, clotting agents, and/or other additives into the inner layer 15 and/or outer layer 20 of the composite 10. The secondary source of injection may take the form of a secondary syringe that connects to the cap 40 to be co-injected with the composite or injected into the bone graft syringe prior to injection of composite. Alternatively, the composite can be soaked or mixed with the additives prior to the composite being positioned in the bone graft syringe.

Methods for Use

In a sterile field, a bone graft syringe comprising a combination of synthetic and allograft or autograft bone is connected to a secondary source containing a stem cell concentrate. The secondary source may take the form of a second syringe. The stem cell concentrate is usually injected into the bone graft syringe from the top and the composite graft absorbs the stem cell concentrate. The bone graft syringe may also be connected to a secondary source for the purposes of injecting platelet rich plasma, bone marrow aspirate, or clotting agent(s). Alternatively, two or more secondary sources may be connected to the bone graft syringe simultaneously. This allows for simultaneous injection of any of the following: platelet rich plasma, bone marrow aspirate, clotting agent(s), and/or other additives. These components may be injected into the bone graft syringe in any order, simultaneously or sequentially. In a preferred embodiment, a Y-shaped adapter is connected to the bone graft syringe to permit the simultaneous injection of stem cell concentrate and a clotting agent until the composite graft is fully saturated.

The bone graft syringe should sit to allow the composite graft to absorb any injected components. The natural "wicking" effect of the materials, combined with injection pressure and gravity, is usually adequate to ensure uniform mixing. Alternatively, a vacuum may be applied to "pull" the injected components into the composite bone graft.

Using the plunger, the composite graft is then expelled and if necessary, may be cut to an appropriate length for clinical application. The composite graft is then topically applied and molded along the posterolateral gutters of the spine, or other areas of the spine to ensure intimate contact to the prepared bone bed across a fusion segment. The composite would typically be used in lumbar regions, and potentially in thoracic regions depending on the circumstances. Multiple composite grafts could be used in a given procedure. The composite grafts could also be applied to an inner space that may be present in certain types of fusion implant devices.

Although illustrative embodiments have been shown and described, a wide range of modifications, changes, and substitutions are contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A composite bone graft comprising:
    an allograft bone component;
    a cylindrical shell; and
    a synthetic bone substitute, wherein the synthetic bone substitute is in contact with the allograft bone component and further comprising a resorbable mesh casing, wherein the composite bone graft is disposed within the resorbable mesh casing and the resorbable mesh casing holds the composite bone graft together and prevents dissipation of the composite bone graft, wherein the composite bone graft is in the form of a cylinder with an inner core and outer layer, and wherein the inner core is disposed within the cylindrical shell and the outer layer is disposed on the outside of the cylindrical shell.

2. The composite of claim 1, wherein the inner core is composed of the allograft bone component and the outer layer is composed of the synthetic bone substitute.

3. The composite of claim 1, wherein the inner core is composed of the synthetic bone substitute and the outer layer is composed of the allograft bone component.

4. The composite of claim 1 wherein the allograft bone component and synthetic bone substitute are at least partially infused with an additive, wherein the additive is one or more of platelet rich plasma, bone marrow aspirate, or stem cells.

5. The composite of claim 1, further comprising a bone graft syringe, wherein the composite bone graft is positioned within the bone graft syringe.

6. The composite of claim 1, wherein the synthetic bone substitute is as beta-tricalcium phosphate, hydroxyapetite, polyglycolic-polylactid acid, or poly-lactic acid; and wherein the allograft bone is in the form of dense cortical bone strips, packed bone chips, or demineralized bone matrix.

7. The composite of claim 1, wherein the inner core is 5 to 15 mm in diameter and the outer layer is 2 to 15 mm in thickness.

* * * * *